(12) United States Patent
Lee et al.

(10) Patent No.: US 10,072,302 B2
(45) Date of Patent: Sep. 11, 2018

(54) CERVICAL CANCER DIAGNOSING METHOD AND DIAGNOSTIC KIT FOR SAME

(71) Applicants: OPTIPHARM. CO., LTD., Cheongju (KR); UNIVERSITY INDUSTRY FOUNDATION, YONSEI UNIVERSITY WONJU CAMPUS, Wonju (KR)

(72) Inventors: Hye Young Lee, Wonju (KR); Hye Young Wang, Gunsan (KR)

(73) Assignees: OPTIPHARM.CO., LTD., Cheongju-si (KR); UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 126 days.

(21) Appl. No.: 15/101,552

(22) PCT Filed: Dec. 5, 2013

(86) PCT No.: PCT/KR2013/011225
§ 371 (c)(1),
(2) Date: Jun. 3, 2016

(87) PCT Pub. No.: WO2015/083852
PCT Pub. Date: Jun. 11, 2015

(65) Prior Publication Data
US 2016/0376662 A1 Dec. 29, 2016

(51) Int. Cl.
*C12Q 1/68* (2018.01)
*C12Q 1/70* (2006.01)
*C12Q 1/6886* (2018.01)

(52) U.S. Cl.
CPC .......... *C12Q 1/6886* (2013.01); *C12Q 1/708* (2013.01); *C12Q 2600/112* (2013.01); *C12Q 2600/118* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 8,980,562 | B1 * | 3/2015 | Manna | C12Q 1/6886 435/6.12 |
| 2005/0118568 | A1 * | 6/2005 | Karlsen | C12Q 1/6886 435/5 |
| 2013/0209987 | A1 * | 8/2013 | Li | C12Q 1/708 435/5 |
| 2013/0309658 | A1 | 11/2013 | Karlsen | |

FOREIGN PATENT DOCUMENTS

| KR | 10-2004-0078506 | 9/2004 |
| KR | 10-2005-0017703 | 2/2005 |
| KR | 10-2013-0125046 | 11/2013 |
| WO | 2010-129941 | 11/2010 |

\* cited by examiner

*Primary Examiner* — David C Thomas
(74) *Attorney, Agent, or Firm* — Lex IP Meister, PLLC

(57) ABSTRACT

There are provided an improved cervical cancer diagnosing method and a diagnostic kit for same. According to the present invention, it is possible to more rapidly and accurately provide a patient group requiring a clinical treatment and a prevention treatment in terms of a technical aspect to predict that the limitation of the existing HPV DNA test method can be overcome, automate the RNA extraction from eliminated cells, and more rapidly provide more objective and accurate results because the result analysis can be performed by software by using the real-time RT-PCR.

5 Claims, 18 Drawing Sheets
Specification includes a Sequence Listing.

[FIG. 1]
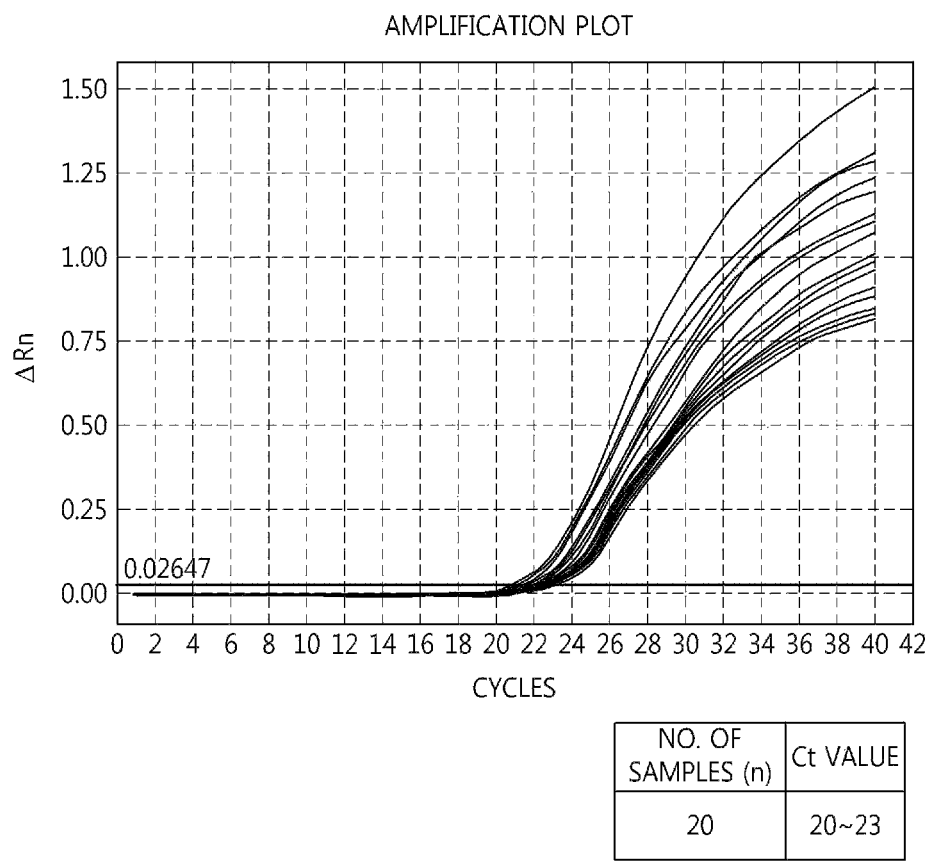

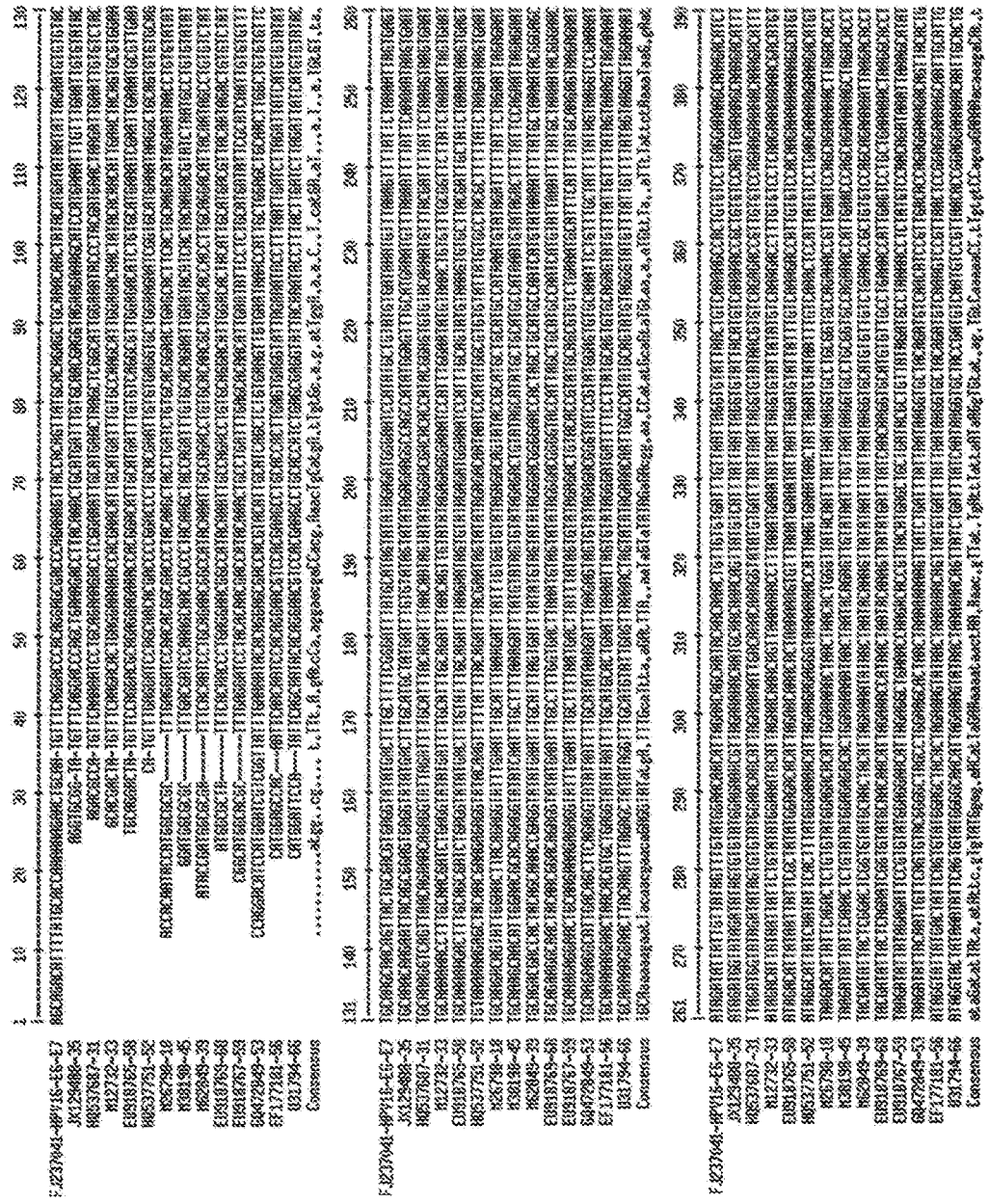
[FIG. 2]

[FIG. 3]

[FIG. 4]
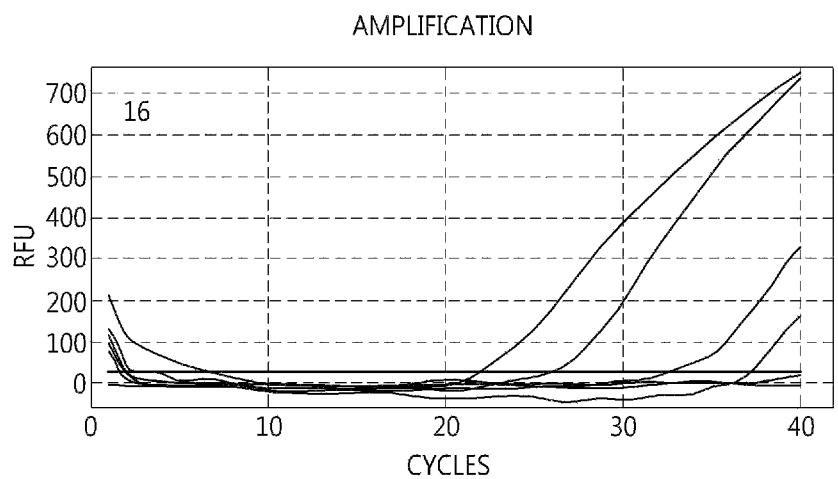
| C03 | FAM | Unkn-16 | 10pg | 22 |
| --- | --- | --- | --- | --- |
| C04 | FAM | Unkn | 1pg | 25.99 |
| C05 | FAM | Unkn | 100fg | 26.82 |
| C06 | FAM | Unkn | 10fg | 33.06 |
| C07 | FAM | Unkn | 1fg | 37.17 |
| C08 | FAM | Unkn | N | N/A |

[FIG. 5]
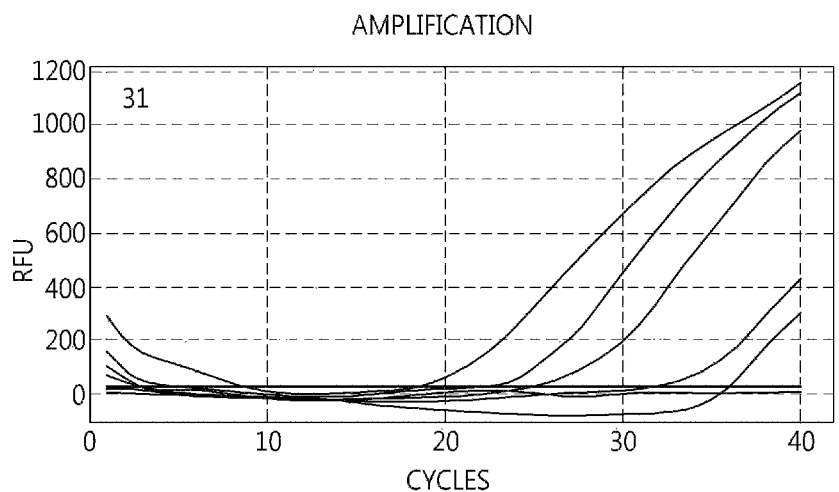
| D03 | FAM | Unkn-31 | 10pg | 18.46 |
| D04 | FAM | Unkn | 1pg | 22.17 |
| D05 | FAM | Unkn | 100fg | 24.27 |
| D06 | FAM | Unkn | 10fg | 31.55 |
| D07 | FAM | Unkn | 1fg | 36 |
| D08 | FAM | Unkn | N | N/A |

[FIG. 6]
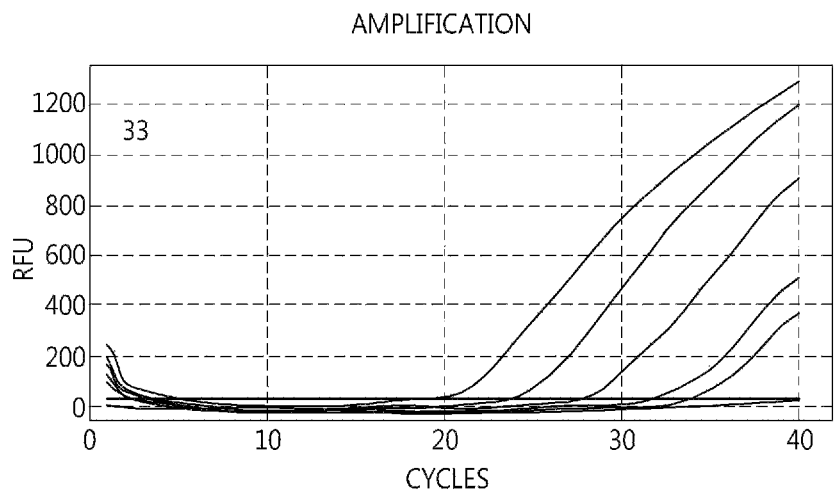
| E03 | FAM | Unkn-33 | 10pg | 19.53 |
| E04 | FAM | Unkn | 1pg | 23.28 |
| E05 | FAM | Unkn | 100fg | 27.23 |
| E06 | FAM | Unkn | 10fg | 31.66 |
| E07 | FAM | Unkn | 1fg | 33.56 |
| E08 | FAM | Unkn | N | N/A |

[FIG. 7]
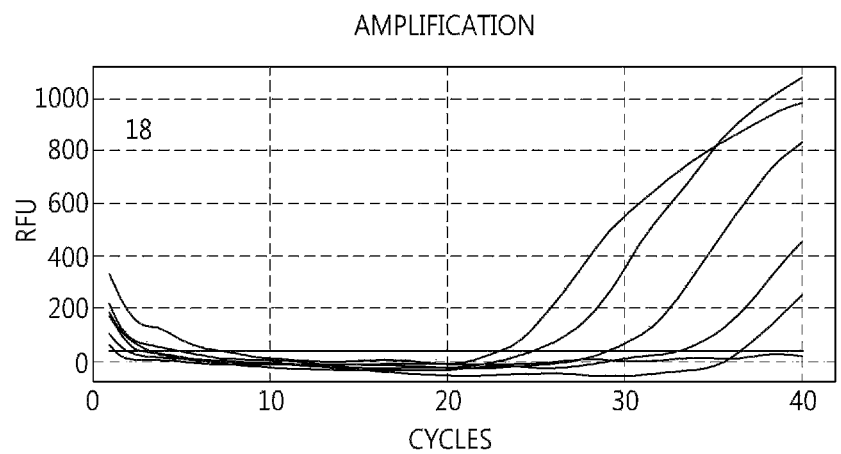
| C03 | FAM | Unkn-18 | 10pg | 21.22 |
| --- | --- | --- | --- | --- |
| C04 | FAM | Unkn | 1pg | 24.63 |
| C05 | FAM | Unkn | 100fg | 29.42 |
| C06 | FAM | Unkn | 10fg | 32.88 |
| C07 | FAM | Unkn | 1fg | 36.92 |
| C08 | FAM | Unkn | N | N/A |

[FIG. 8]
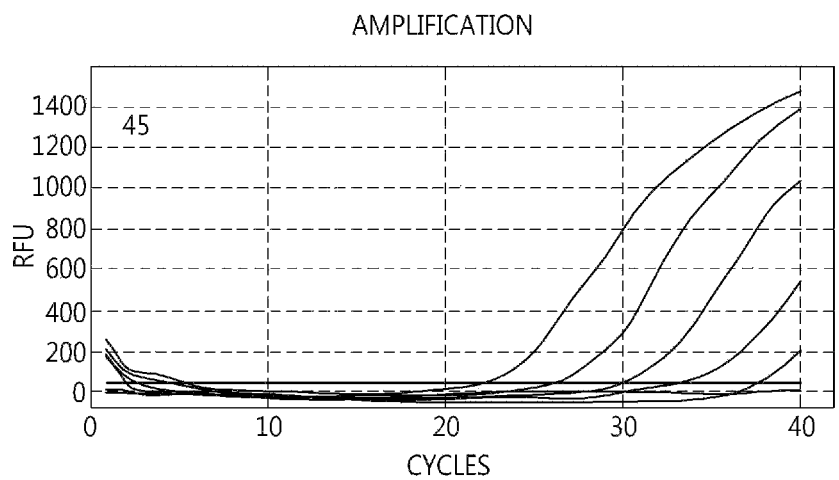
| E03 | FAM | Unkn-45 | 10pg | 21.62 |
| E04 | FAM | Unkn | 1pg | 26.02 |
| E05 | FAM | Unkn | 100fg | 29.84 |
| E06 | FAM | Unkn | 10fg | 32.51 |
| E07 | FAM | Unkn | 1fg | 37.5 |
| E08 | FAM | Unkn | N | N/A |

[FIG. 9]
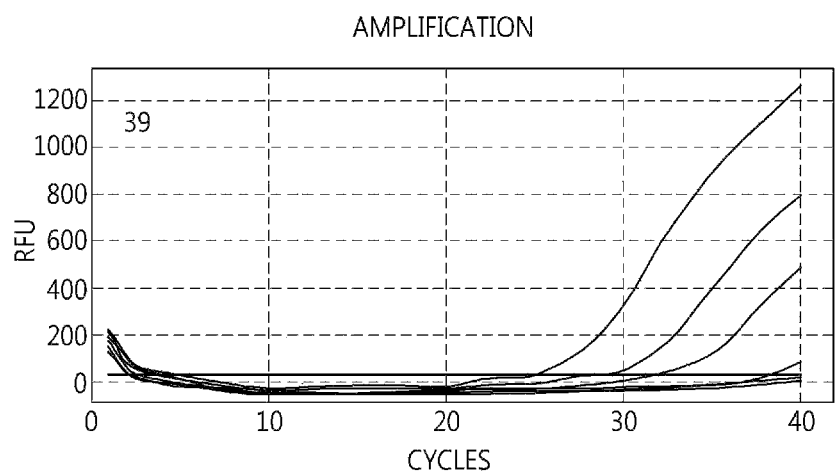

[FIG. 10]
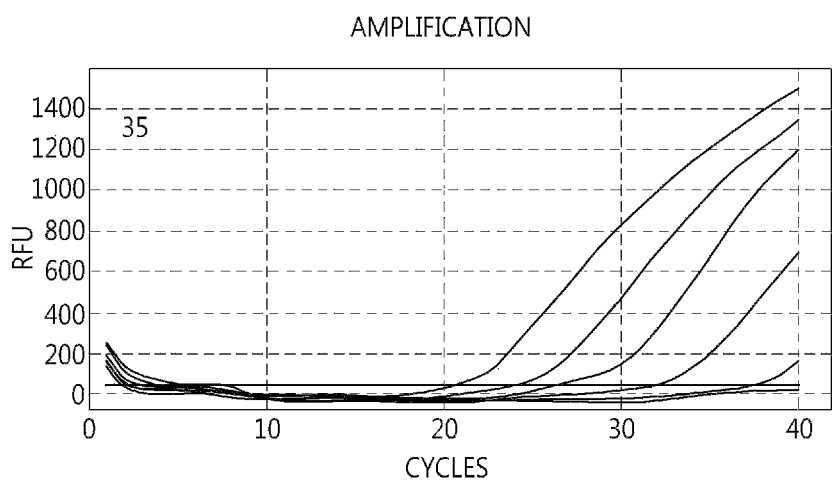
| C03 | FAM | Unkn-35 | 10pg | 20.37 |
| C04 | FAM | Unkn | 1pg | 23.74 |
| C05 | FAM | Unkn | 100fg | 26.06 |
| C06 | FAM | Unkn | 10fg | 30.94 |
| C07 | FAM | Unkn | 1fg | 37.5 |
| C08 | FAM | Unkn | N | N/A |

[FIG. 11]
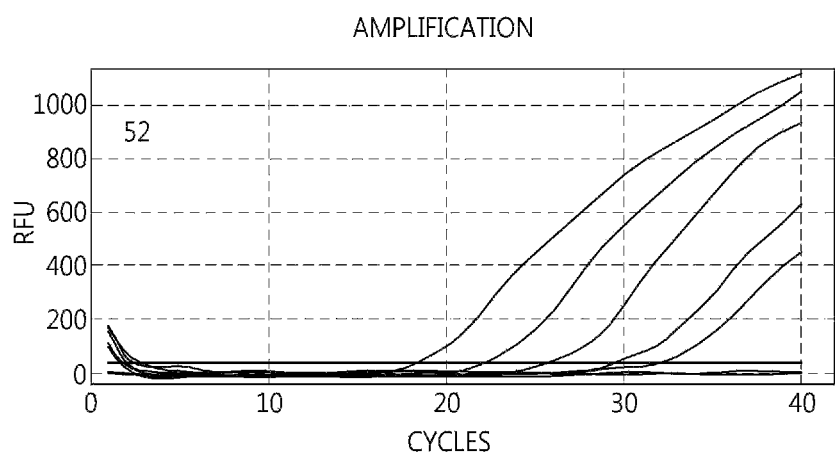
| G03 | FAM | Unkn-52 | 10pg | 17.7 |
| G04 | FAM | Unkn | 1pg | 21.71 |
| G05 | FAM | Unkn | 100fg | 25.69 |
| G06 | FAM | Unkn | 10fg | 29.01 |
| G07 | FAM | Unkn | 1fg | 31.16 |
| G08 | FAM | Unkn | N | N/A |

[FIG. 12]
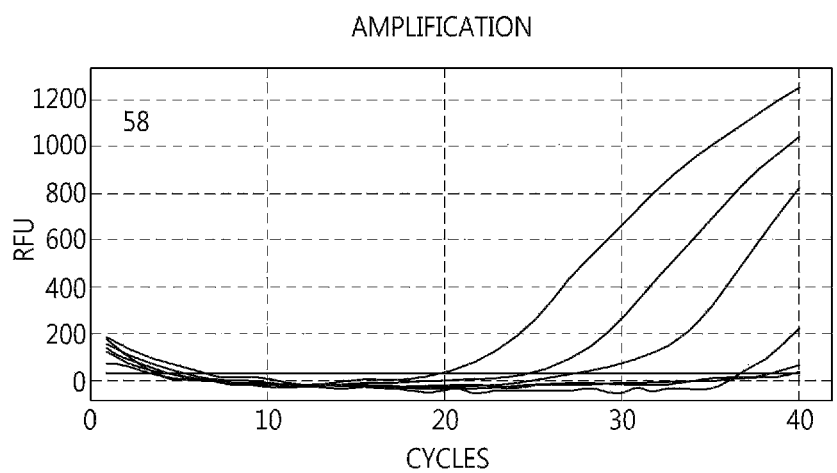
| H03 | FAM | Unkn-58 | 10pg | 19.76 |
| H04 | FAM | Unkn | 1pg | 24.46 |
| H05 | FAM | Unkn | 100fg | 27.41 |
| H06 | FAM | Unkn | 10fg | 36.87 |
| H07 | FAM | Unkn | 1fg | 38.3 |
| H08 | FAM | Unkn | N | N/A |

[FIG. 13]
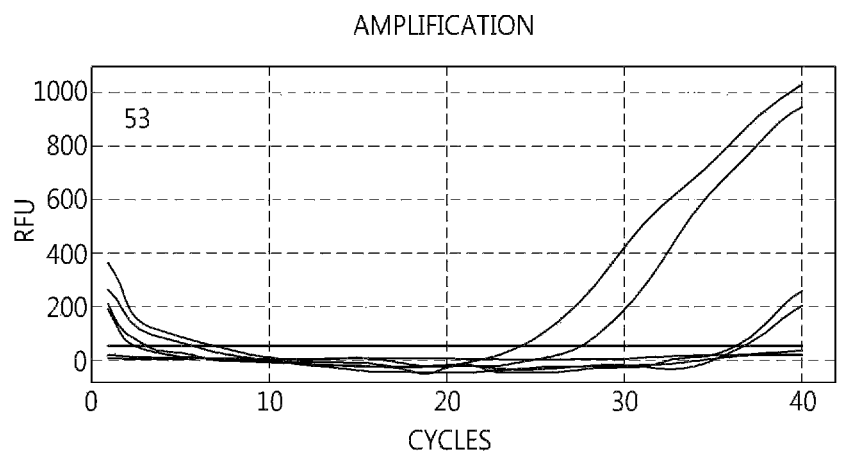
| E03 | FAM | Unkn-53 | 10pg | 24.29 |
| E04 | FAM | Unkn | 1pg | 27.63 |
| E05 | FAM | Unkn | 100fg | 31.26 |
| E06 | FAM | Unkn | 10fg | 37 |
| E07 | FAM | Unkn | 1fg | 37.06 |
| E08 | FAM | Unkn | N | N/A |

[FIG. 14]
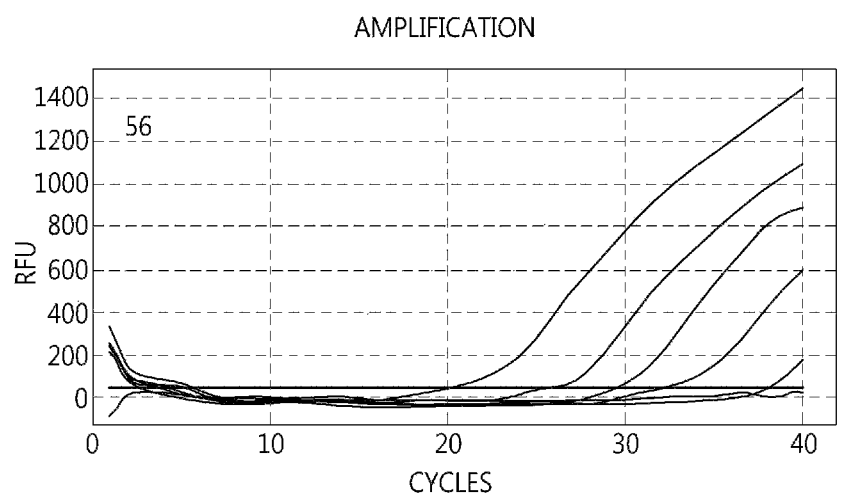

[FIG. 15]
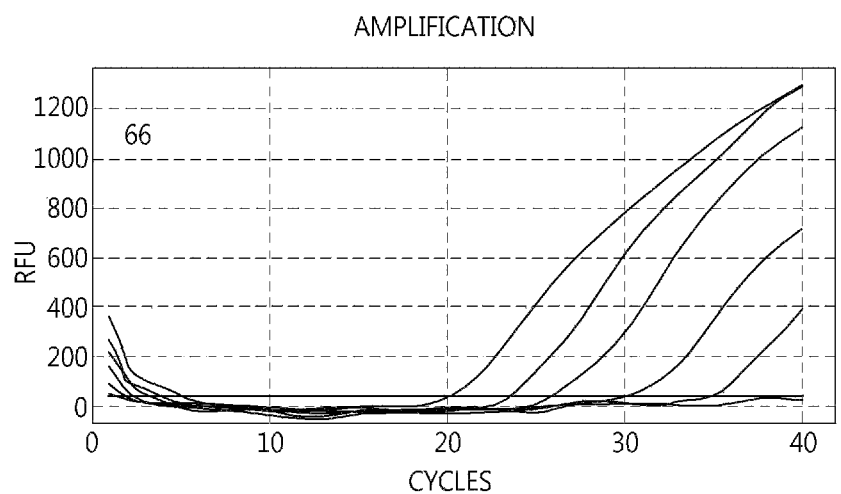
| G03 | FAM | Unkn-66 | 10pg | 20.14 |
| G04 | FAM | Unkn | 1pg | 23.58 |
| G05 | FAM | Unkn | 100fg | 25.27 |
| G06 | FAM | Unkn | 10fg | 30.19 |
| G07 | FAM | Unkn | 1fg | 34.94 |
| G08 | FAM | Unkn | N | N/A |

[FIG. 16]
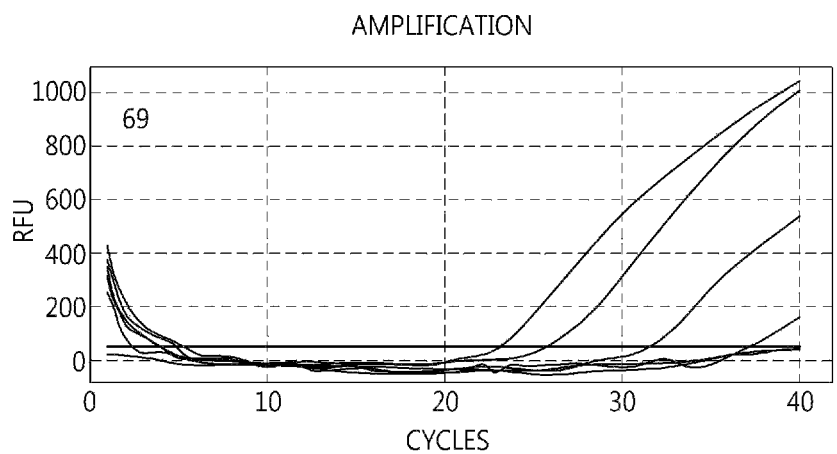

[FIG. 17]
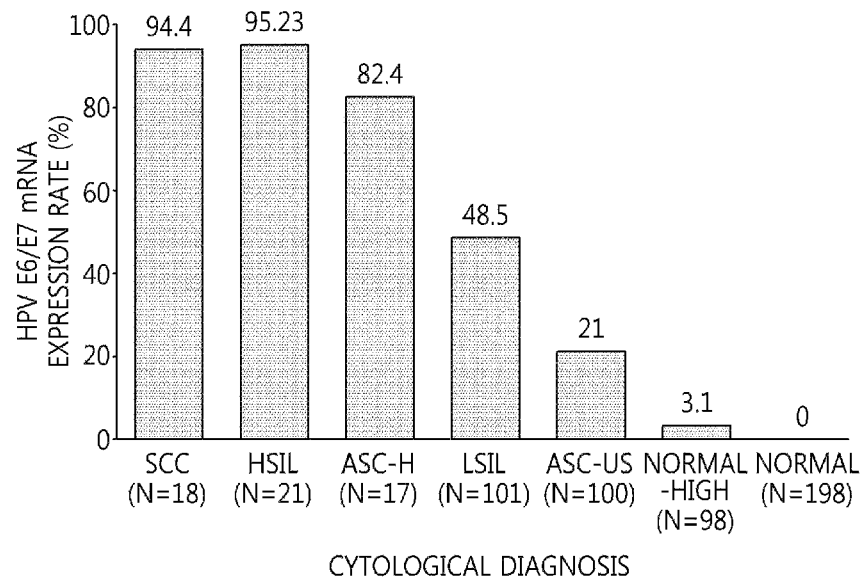
[FIG. 18]
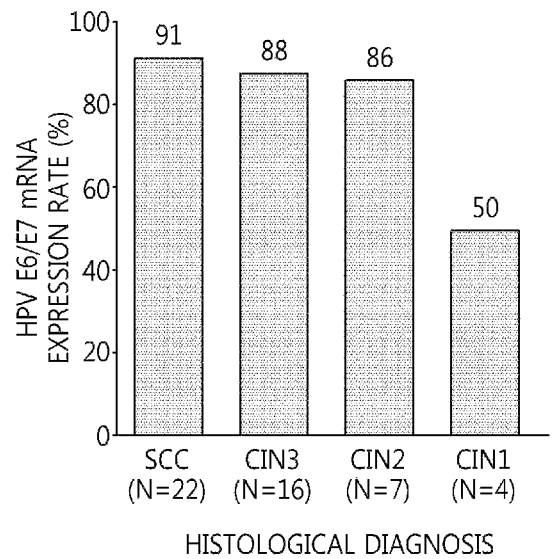

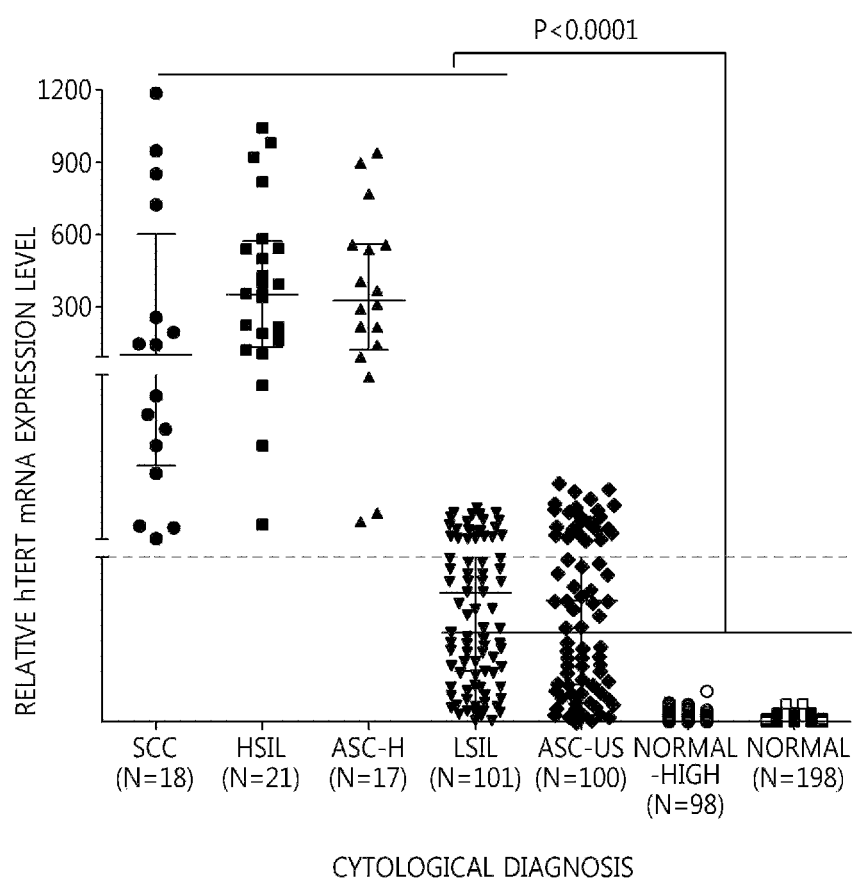
[FIG. 19]

CERVICAL CANCER DIAGNOSING METHOD AND DIAGNOSTIC KIT FOR SAME

TECHNICAL FIELD

The present invention relates to an improved cervical cancer diagnosing method and a diagnostic kit for the same.

BACKGROUND ART

Cervical cancer is the second most common cancer among women throughout the world (Ferlay J, Shin H R, Bray F, Forman D, Mathers C, Parkin D M. Int J Cancer. 2010. 127: 2893-2917.), the 5-year survival rate of the cervical cancer is about 80% or more by the national cancer registration program, and thus, it is known that the cancer is detected early and the survival rate is increased. It is found that Human Papillomavirus (HPV) is present in 99.7% of cervical cancer patients, and it is known that the survival of the HPB infection causes transition to invasive cervical cancer and cervical precancers.

Currently, it is known that gene types of HPV are 100 or more types and gene types causing diseases to the human among them are about 30 types. The gene types causing diseases to the human are classified into high-risk groups 16, 18, 31, 33, 35, 39, 45, 51, 52, 56, 58, 59, 68, 73, and 82, low-risk groups 6, 11, 40, 42, 43, 44, 54, 61, 70, 72, and 81, and potential-risk groups 34, 57, and 83. HPV having each gene type is discovered specifically according to location of lesions and progression of the lesion and thus, the biological diversity of HPV infection has been recognized.

The most common method for diagnosing infection of the HPV is a cervical papanicolaou smear (hereinafter, a Pap smearing test) that performs a cell diagnostic test by using the eliminated cells obtained from the cervix, and it was known that the test method has high availability as a cervical cancer selection test due to economic reasons in which a testing method is simple and cost is low, but there is a disadvantage in that the sensitivity is approximately 20~50% and the false negative rate is very high (Hwang T S, Jeong J K, Park M, Han H S, Choi H K, Park T S. Gynecol Oncol. 2003. 90: 51-56). Particularly, low sensitivity and predictive value for high-grade squamous intraepithelial lesion (hereinafter, referred to as HSIL) are reported, and as compared with squamous cell carcinoma, due to low selection for grandular lesion or adenocarcinoma, it is difficult to initial-diagnose the cervical cancer, and thus, there are many limitations in the Pap smearing test in the cervical cancer diagnosis (Kim Y S, Lee H J, Lee G G. Korean J. Clin. Pathol. 2001. 21: 210-214; Kwon H S, Kim Y T, Kim J W, Kim S H. Korean J Gynecol Oncol Colposc. 2002. 13: 327-335.).

Further, a test method using a colposcope may obtain an accurate result compared with the Pap smear test, but requires skilled technicians and expensive equipment, and there is a disadvantage in that the infection of HPV cannot be distinguished.

In the process to progress to the cervical cancer, as the HPV is known as an important factor, it is important to find a presence of HPV DNA in the initial diagnosis of the cervical cancer in addition to the Pap test as a cytological test method which has been used in the existing cervical cancer test.

As it is known that the progressing to the cervical cancer was associated with the infection of human papillomavirus (hereinafter, referred to as HPV), many HPV DNA test methods including an HPV gene type testing method of testing HPV gene types based on an L1 gene coding a capsid protein from a method of detecting a HPV DNA from the cervix have been developed and commercialized. Currently, the molecular diagnostic methods have been used together as an assisting test of the Pap smear test (Thomas I, Liesje G, Ryan S. J Clin Microbiol. 1999. 37: 2508-2517). The use is also increased in Korea (Cho E J, Do J H, Kim Y S, Bae S, Ahn W S. J Med Microbiol. 2011. 60: 162-171).

As the HPV DNA test method, representatively, a method of finding a presence of DNA of HPV by using polymerase chain reaction (PCR) or a method of testing gene types of HPV by using a DNA chip or a reverse blot hybridization assay (REBA) is known.

In the HPV DNA test and the HPV Genotyping test, it is advantageous that the sensitivity is very high and the infected HPV gene type can be known, but there is a limit that the analytical sensitivity is too high and thus even in low-grade lesion and normal opinions as well as the high-grade lesions SCC and HSIL, it is detected at a high ratio of approximately 40 to 50%. The HVP infection can be detected by only the presence of the HPV DNA, but there is a disadvantage in that the cervical cancer may not be immediately diagnosed.

When the cervix is infected with the HPV, the HPV oncogenes E6/E7 are overexpressed and a function of a cancer suppressor protein such as p53 and pRB is inhibited to cause the cancer.

However, according to recent studies for some years, even in the inflammation step before generating the cancer or a normal cervix as well as a cervical cancer patient, the HPV DNA positive rate is too high, and thus, even though the HPV DNA is detected, it is difficult to treat and prevent the clinical cervical cancer.

Meantime, in order to detect the HPV DNA and the gene types, a site encoding a L1 (late gene 1) capsid protein having the largest size in the nucleic acid of the HPV has been developed as a target, but detecting the gene expression level by targeting mRNA encoding E6/E7 as the protein expressed when inducing the cancer is more available than determining cervical cancer or a prognosis of the cervical cancer.

Until now, the development of the HPV mRNA test method which targets the HPV oncogenes E6, E7 mRNA is slight in Korea, and in the domestic medium and large hospitals, the HPV DNA gene type tests have been increased. However, the HPV DNA positive rate is high in the cervical cancer and in normal, and thus, it is difficult to be immediately applied to direct clinical treatment or prevention treatment.

Recently, a test method of targeting mRNA encoding E6 and E7 genes as the oncogenes in an HPV high-risk group other than the test using the DNA of the HPV has been developed and a real-time NASBA test method that may detect the E6, E7 mRNA of HPV 16, 18, 31, 33, 45 gene types which are most present in the cervical cancer was already commercialized worldwide. However, the test kits are too expensive (price: 30,000 won/test), and for the real-time NASBA, a dedicated analysis machine is required. However, in the current medium and large hospitals, the dedicated analysis machine is not possessed and thus, substantially, it is difficult to be applied to the clinical test. Further, in the case of the current commercialized E6, E7 mRNA test method, since 5 HPV gene types HPV 16, 18, 31, 33, and 45 which are pandemic worldwide are included, the HPV gene types had a difference from the HPV gene types separated from the cervical cancer caused in Korea, and thus, there is a limit to apply the method to domestic patients.

PRIOR DOCUMENT

Korea Patent Publication No. 1020040078506

DISCLOSURE

Technical Problem

In order to solve the conventional problems, an object of the present invention is to provide an improved cervical cancer diagnosing method which is rapid and accurate.

Another object of the present invention is to provide an improved cervical cancer diagnosis kit which is rapid and accurate.

Technical Solution

In order to achieve the above object, an exemplary embodiment of the present invention provides an information providing method for diagnosing cervical cancer comprising: a) separating a total RNA from cells obtained from a patient's blood; b) synthesizing cDNA from the separated total RNA; c) performing real-time-PCR for the synthesized cDNA by using a primer set and a probe capable of amplifying HPV types 16, 35, 31, 58, 33, and 52; a primer set and a probe capable of amplifying HPV types 18, 45, 39, 68, and 59; a primer set and a probe capable of amplifying HPV types 53, 56, 66, 51, 69, 26, and 30; and a primer set and a probe capable of amplifying glyceraldehyde 3-phosphate dehydrogenase (GAPDH) and human telomerase reverse transcriptase (hTERT) genes; and d) comparing the expressed level with an expressed level in a normal person.

The method of separating the total RNA and the method of synthesizing cDNA from the separated total RNA which are generally used may be performed through known methods, and the detailed description for the process is described in Joseph Sambrook et al., Molecular Cloning, A Laboratory Manual, Cold Spring Harbor Laboratory Press, Cold Spring Harbor, N.Y. (2001); Noonan, K. F., and the like and may be inserted as the reference of the present invention.

The primer of the present invention may be chemically synthesized by using a phosphoramidite solid support method or other well-known methods. The nucleic acid sequence may be modified by using many means known in the art. As an unlimited example of the modification, there are methylation, "capsulation", substitution to analogues of one or more natural nucleotides, and modification between nucleotides, for example, modification to a non-charged connection body (For example, methyl phosphonate, phosphotriester, phospho amidate, carbamates, etc.) or a charged connection body (for example, phosphorothioate, phosphorodithioate, etc.). The nucleic acid may contain one or more additional covalently-linked residues, for example, a protein (e.g., nucleases, toxins, antibodies, signal peptides, poly-L-lysine, etc.), an intercalating agent (e.g., acridine, psoralen, etc.), a chelating agent (e.g., metal, radioactive metal, iron, oxidative metal, etc.), and an alkylating agent. The nucleic acid sequence of the present invention may be modified by using a marker which may directly or indirectly provide a detectable signal. An example of the marker includes a radioisotope, a fluorescent molecule, biotin, or the like.

In the method of the present invention, the amplified target sequence may be marked as a detectable marking material. In an exemplary embodiment, the marking material may be a fluorescent, phosphorescent, chemiluminescent, or radioactive material, but the present invention is not limited thereto. Preferably, the marking material may be fluorescein, phycoerythrin, rhodamine, lissamine, Cy-5 or Cy-3. When real-time RT-PCR is performed by marking Cy-5 or Cy-3 in a 5'-terminal and/or a 3'-terminal of the primer when amplifying the target sequence, the target sequence may be marked with the detectable fluorescent marking material.

Further, in the marker using the radioactive material, when the radioactive isotope such as 32P or 35S during the real-time RT-PCR is added in a PCR reaction solution, the amplified production is synthesized and the radioactive material is inserted to the amplified product, and thus, the amplified product may be marked with the radioactive material. One or more oligonucleotide primer sets used for amplifying the target sequence may be used.

The marking may be performed by various methods which are generally performed in the art, for example, a nick translation method, a random priming method Multiprime DNA labelling systems booklet, "Amersham" (1989)), and a KaiNation method Maxam & Gilbert, Methods in Enzymology, 65:499(1986)). The marking provides a signal which is detectable by fluorescence, radioactivity, color measurement, weight measurement, X-ray diffraction or absorption, magnetism, enzymatic activity, mass analysis, binding affinity, hybridization high frequency, and nanocrystalline.

According to an aspect of the present invention, in the present invention, an expression level at an mRNA level is measured through RT-PCR. To this end, a new primer set which is specifically bound to the HPV gene and a probe marked with fluorescence are required, and in the present invention, the corresponding primer and probe specified with a specific base sequence may be used, but the present invention is not limited thereto. The primer and probe may be used without limitation so long as performing the real-time RT-PCR by providing a detectable signal which is specifically bound to the genes. Herein, FAM and Quen (Quencher) mean fluorescent dyes.

The real-time RT-PCR method applied to the present invention may be performed through a known process which is generally used in the art.

The process of measuring the mRNA expression level may be used with limitation as long as measuring the mRNA expression level and may be performed through radiation measurement, fluorescence measurement or phosphorescence measurement according to a kind of used probe marker, but the present invention is not limited thereto. As one of the method of detecting the amplified product, in the fluorescence measurement method, when the real-time RT-PCR is performed by marking Cy-5 or Cy-3 in the 5'-terminal of the primer, the target sequence is marked with a detectable fluorescent marker, and the marked fluorescence may be measured by using a fluorescence meter. Further, in the radioactive measurement method, when the real-time RT-PCR is performed, after the amplified product is marked by adding the radioisotope such as $^{32}$P or $^{35}$S in a PCR reaction solution, the radioactive material may be measured by using radiation measuring equipment, for example, a Geiger counter or a liquid scintillation counter.

According to an exemplary embodiment of the present invention, the probe marked with the fluorescence is attached to the PCR product amplified through the real-time RT-PCR to emit fluorescence having a specific wavelength. Simultaneously with amplification, in the fluorescence meter of the real-time PCR device, the mRNA expression level of the genes of the present invention is measured in real time, the measured value is calculated and visualized through PC and thus, a checker may easily check the expression level.

In an exemplary embodiment of the present invention, preferably, the primer set capable of amplifying the HPV types 16, 35, 31, 58, 33, and 52 are represented by SEQ ID NOS: 1 and 2 and the probe has a base sequence represented by SEQ ID NO: 3.

In another exemplary embodiment of the present invention, preferably, the primer set capable of amplifying the HPV types 18, 45, 39, 68, and 59 are represented by SEQ ID NOS: 4 to 7 and the probe has a base sequence represented by SEQ ID NO: 8.

In yet another exemplary embodiment of the present invention, preferably, the primer set capable of amplifying the HPV types 53, 56, 66, 51, 69, 26, and 30 are represented by SEQ ID NOS: 9 and 10 or 12 and 13 and the probe has a base sequence represented by SEQ ID NO: 11 or 14.

In still another exemplary embodiment of the present invention, preferably, the primer set capable of amplifying the GAPDH gene are represented by SEQ ID NOS: 15 and 16 and the probe has a base sequence represented by SEQ ID NO: 17, and the primer set capable of amplifying the hTERT gene are represented by SEQ ID NOS: 18 and 19 and the probe has a base sequence represented by SEQ ID NO: 20, but the present invention is not limited thereto.

Further, the present invention provides a composition of a primer set and a probe for diagnosing cervical cancer, comprising: a primer set represented by SEQ ID NOS: 1 and 2 and a probe having a base sequence represented by SEQ ID NO: 3 which amplify HPV types 16, 35, 31, 58, 33, and 52; a primer set represented by SEQ ID NOS: 4 to 7 and a probe having a base sequence represented by SEQ ID NO: 8 which amplify HPV types 18, 45, 39, 68, and 59; a primer set represented by SEQ ID NOS: 9 and 10 or 12 and 13 and a probe having a base sequence represented by SEQ ID NO: 11 or 14 which amplify HPV types 53, 56, 66, 51, 69, 26, and 30; and a primer set represented by SEQ ID NOS: 15 and 16 and a probe having a base sequence represented by SEQ ID NO: 17 which amplify a GAPDH gene and a primer set represented by SEQ ID NOS: 18 and 19 and a probe having a base sequence represented by SEQ ID NO: 20 which amplify a hTERT gene.

Also, the present invention provides a composition for diagnosing cervical cancer containing the composition of the primer set and the probe as an active ingredient.

Also, the present invention provides a kit for diagnosing cervical cancer containing the composition.

According to another aspect of the present invention, the diagnosis kit may be a cancer diagnosis kit comprising a required element required for performing a reverse transcription polymerase reaction. The reverse transcription polymerase reaction kit may include each gene-specific primer set of the present invention. The primer is a nucleotide having a specific sequence to a nucleic acid sequence of the maker gene and may have a length of approximately 7 bp to 50 bp and more preferably approximately 10 bp to 30 bp, and more preferably, the diagnosis kit may include a new primer set represented by a sequence number of the present invention and a fluorescence-marked probe.

Other reverse transcription polymerase reaction kits may include a test tube or another suitable container, a reaction buffer (pH and magnesium concentration are varied), deoxynucleotide (dNTPs), enzymes such as Taq-polymerase and reverse transcriptase, DNAse, RNAse inhibitor, DEPC-water, sterile water, and the like.

In the present invention, the term "information providing method for cancer diagnosis" is to provide objective basic information required for the diagnosis of cancer as a preliminary step and clinical determination or opinions of doctors are excluded.

The term "primer" means a short nucleic acid sequence which may form a complementary template and a base pair as a nucleic acid sequence having a short free 3-terminal hydroxyl group and serves as a starting point for duplicating the template strand. The primer may initiate DNA synthesis under a presence of a reagent for polymerization (that is, DNA polymerase or reverse transcriptase) and four different nucleoside triphosphates in a suitable buffer solution and temperature. The primer of the present invention is sense or antisense nucleic acid having 7 to 50 nucleotide sequences as a marker gene-specific primer. The primer may combine an additional feature without changing a basic property of the primer acting as an initial point of the DNA synthesis.

The term "probe" is a single chain nucleic acid molecule and includes a complementary sequence to a target nucleic acid sequence.

The term 'real-time RT-PCR" is a molecular polymerization method of reverse-transcribing RNA to complementary DNA (cDNA) by using a reverse transcriptase, amplifying a target by using a target probe including a target primer and a marker by using the made CDNA as a template, and simultaneously, quantitively detecting a signal generated in the marker of the target probe in the amplified target.

Hereinafter, the present invention will be described.

In the present invention, in addition to HPV 16, 18, 31, 33, 45 gene types which are known to be associated with cervical cancer in worldwide, HPV 35, 52, 56, 58, 39, 51, 59, 68, 53, 66, 69 gene types which are known to be associated with cervical cancer in Korea and neighboring nations thereof are targeted. A test method to enhance the positive rate of cervical cancer diagnosis and help in treatment and diagnosis as a prognostic factor that may progress to the cancer will be developed by adding a telomerase (hTERT) real-time PCR test method for false negative samples which are not shown through expression of HPV E6, E7 genes as well as a Multiplex real-time RT-PCR test method using a TaqMan probe suitable for a domestic situation which may accurately measure the mRNA expression of E6, E7 oncogenes.

Effect

According to the present invention, it is possible to more rapidly and accurately provide a patient group requiring a clinical treatment and a prevention treatment in terms of a technical aspect to predict that the limitation of the existing HPV DNA test method can be overcome, automate the RNA extraction from eliminated cells, and more rapidly provide more objective and accurate results because the result analysis can be performed by software by using the real-time RT-PCR.

DESCRIPTION OF DRAWINGS

FIG. 1 illustrates a GAPDH mRNA real-time RT-PCR result of a clinical specimen.

Figure 3:
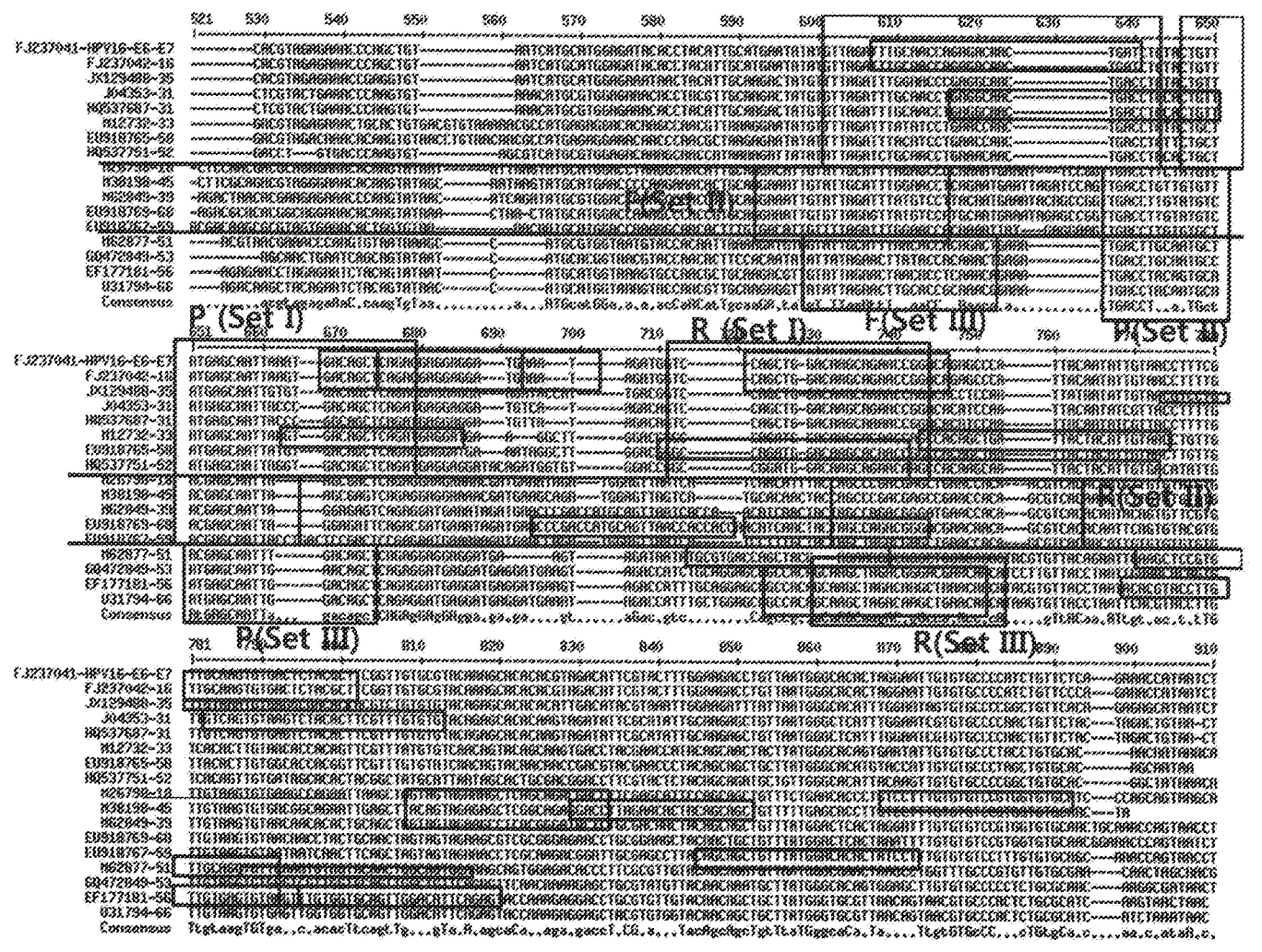

FIGS. 2 and 3 illustrate an analysis of E6/E7 standard base sequences and primers of 16 kinds of HPVs in a main high-risk group, and TaqMan probe positions.

FIGS. 4 to 16 illustrate sensitivity in E6/7 using HPV mRNA.

FIGS. 17 and 18 illustrate HPV E6/E7 positive detection frequency according to cytopathological (A) and histological (B) classifications by a multiplex RT-PCR method.

FIG. 19 illustrates an expression profile (high-level lesion (SCC, HSIL, ASC-H) and low-level lesion (LSIL, ASC-US)) of hTERT mRNA according to a cytopathological classification using liquid cervical cells.

BEST MODE

Hereinafter, the present invention will be described in more detail with reference to unlimited Examples. However, the following Examples are described for exemplifying the present invention and it is not understood that the scope of the present invention is limited to the following Examples.

EXAMPLE 1

Collection and Securement of Clinical Specimen

Remaining cervical eliminated cells of a patient which was subjected to a cervical liquid cell test (Thin Prep PAP TEST, PreservCyt Solution, Hologic Inc. Marlborough, Mass., USA) from the department of pathology of Wonju Christian hospital of Yonsei University were stored in 100% anhydrous ethanol for RNA extraction, collected, and secured.

EXAMPLE 2

Entire RNA Extraction from Clinical Specimen (Cervical Eliminated Cells

In order to separate the entire RNA from the clinical specimen, MagNA Pure LC 2.0(Roche) and MagNA Pure LC RNA Isolation Kit High Performance (Roche) as automatic nucleic acid extraction equipment were used. The entire separate RNA was quantified by using a NanoQuant system (TECAN).

EXAMPLE 3

Synthesis of cDNA from Extracted Entire RAN

2 µg of the entire RNA separated from the clinical specimen, 0.25 µg of random primer (Invitrogen), 250 µM of dNTP (Cosmo gene tech), Tris-HCl (pH 8.3) 50 mM, KCl 75 mM, $MgCl_2$ 3 mM, DTT 8 mM, and MMLV reverse transcription polymerase 200 units (Invitrogen) were added and mixed with DEPC-treated DW to have 20 µl of a final volume, and then reacted with a synthesis reaction solution for 10 min at 25° C., for 50 min at 37° C., and for 15 min at 70° C. in thermocycler (ABI) to synthesize cDNA. In order to verify whether the synthesized cDNA was suitable to perform a real-time RT-PCR, the real-time RT-PCR was performed by setting human glyceraldehyde 3-phosphate dehydrogenase (GAPDH) as an endogenous control, and as a result, it was verified that the synthesized cDNA extracted from the clinical specimen was suitable to be used in the present invention (see FIG. 1).

EXAMPLE 4

Analysis of E6/E7 mRNA Base Sequences, Primers, and TaqMan Probe Designs of 16 Main HPV Gene Types in High-Risk Group for Multiplex RT-qPCR E6/E7 mRNA base sequences of 16 main HPV gene types in high-risk group which was the most common cervical cancer were secured based on NCBI standard base sequences, and in the base sequences, appropriate primers and TaqMan probe positions were selected through a multi-align system and designed.

TABLE 1

| | | | |
|---|---|---|---|
| Set I detection type | 16, 35, 31, 58, 33, 52 | | |
| F1 | TTAGATTTRBADCCH GARVCAACTGAYCT (SEQ ID NO: 1) | 10 p | |
| R1 | CYGGTTBTGCTTGTC CAKCTGG (SEQ ID NO: 2) | 10 p | |
| P1-2 | CTGYTATGAGCAATT RNVYGRCAGCTCAGA (SEQ ID NO: 3) | 10 p | FAM-BHQ1 |
| Set II detection type | 18, 45, 39, 68, 59 | | |
| F2-2 | GAMATTGTDTTRSAT TTRKRDCC (SEQ ID NO: 4) | 10 p | |
| F2-3 | TGCARGAMATTGTRT TRSAKTT (SEQ ID NO: 5) | 10 p | |
| F2-4 | TGCARGAMATTGTDT TRSAKTTRKRDCC (SEQ ID NO: 6) | 10 p | |
| R2-1 | TGTGACGYTGTKGTT CRKCYCGTCKRGCT (SEQ ID NO: 7) | 10 p | |
| P2-4 | TTGACCTKBTRTGYY ACGAGCAATT (SEQ ID NO: 8) | 10 p | Cy5-BHQ2 |
| Set III detection type | 53, 56, 66, 51, 69, 26, 30 | | |
| F3-1 | TRTWTTAGAACTDRY ACCDCAAAC (SEQ ID NO: 9) | 10 p | |
| R3-2 | GTCTAYTTCATCCTC ATCCTCYTCCTCTG (λ-] SEQ ID NO: 10) | 10 p | |
| P3-3 | TTGACCTRCADTGCH ATGAGCAATTGRAC (SEQ ID NO: 11) | 10 p | HEX-BHQ1 |
| 51-69F | GATGTWRTATTRSAT TTRRYRCC (SEQ ID NO: 12) | 10 p | |
| 26-51-69R | ACGCAYATTATCTRY TTCATCCTCMTC (SEQ ID NO: 13) | 10 p | |
| 51-69-P | TTGACYTRCAVTGYT ACGARCAATTKGAC (SEQ ID NO: 14) | 10 p | HEX-BHQ1 |
| GAPDH-F | CCATCTTCCAGGAGC GAGATCC (SEQ ID NO: 15) | 10 p | |

TABLE 1-continued

| | | | |
|---|---|---|---|
| GAPDH-R | ATGGTGGTGAAGACG CCAGTG (SEQ ID NO: 16) | 10 p | |
| GAPDH-P | TCCACGACGTACTCA GCGCCAGCA (SEQ ID NO: 17) | 10 p | Cy5- BHQ2 |
| hTERT-F | TGACGTCCAGACTCC GCTTCAT (SEQ ID NO: 18) | 10 p | |
| hTERT-R | TTCTGGCTCCCACGA CGTAGTCC (SEQ ID NO: 19) | 10 p | |
| hTERT-P | ACGGGCTGCGGCCGA TTGTGAACAT (SEQ ID NO: 20) | 10 p | FAM- BHQ1 |

Table 1 illustrates primers and probe sequences used in the present invention.

EXAMPLE 5

Performance of RT-qPCR

A composition of a reactant of Real-time PCR was prepared by adding 25 mM TAPS (pH 9.3 at 25° C.), 50 mM KCl, 2 mM $MgCl_2$, 1 mM 2-mercaptoethanol, 200 µM each dNTP, and 1 unit Taq polymerase (TAKARA), adding 10 pmole of a forward primer and a reverse primer in Table 1, respectively, adding 10 pmole of probe, and adding 2 µl of the synthesized cDNA to have a final volume of 20 µl. PCR reaction was performed for 5 min at a denaturation temperature of 94° C. by using CFX 96 (BioRad-USA) one time and repetitively performed 40 times on a cycle of 30 sec at a denaturation temperature of 95° C. and 20 sec at an annealing temperature of 55° C. Further, a process of measuring fluorescence was added after each annealing process to measure an increased fluorescence value for each cycle.

EXAMPLE 6

Analysis of Result

The result of each test was analyzed by using CFX Manager software v1.6 (Bio-rad). In the case of HPV E6/7 mRNA PCR, when the Ct value was 35 or less, it was determined as positive, and when the Ct value was 35 or more, it was determined as negative. In the case of a hTERT marker, an expression level in a patient group was compared and quantified based on the expression level of GAPDH to check the expression rate.

EXAMPLE 7

Verification of Amplification Through Software Analysis and Quantification of Amplified Product An expression level of a specific gene of qRT-PCR was measured based on the following Relational Formula by using a comparative Ct method which was one of the quantifying methods and the Formula was embedded in Bio-Rad CFX Manager Software and automatically calculated.

[Relational Formula 1]

$\Delta\Delta Ct = \Delta Ct$(sample)$-\Delta Ct$(reference gene)

Herein, the Ct value represented a value of cycle in which amplification started to be distinctly increased during the PCR process.

ΔΔCt means a mRNA expression ratio of a vertical axis in FIG. 4 below.

[Relational Formula 2]

Relational Formula of expression level analysis of hTERT in positive control group $\Delta Ct$ value of SKBR3=$Ct$ value of HER2 in SKBR3− $Ct$ value of reference gene (GAPDH) in SKBR3

$\Delta Ct$ value of THP-1=$Ct$ value of HER2 in THP-1− $Ct$ value of reference gene (GAPDH) in THP-1

$R$ (expression level)=$\Delta Ct$ value of SKBR3−$\Delta Ct$ value of THP-1

[Relational Formula 3]

Relational Formula of expression level analysis of hTERT for tissue sample of cervical cancer patient $\Delta Ct$ value in cervical cancer patient's tissue=$Ct$ value of hTERT in cervical cancer patient's tissue−$Ct$ value of reference(GAPDH)gene in tissue $\Delta Ct$ value of THP-1=$Ct$ value of HER2 in THP-1− $Ct$ value of reference gene (GAPDH) in THP-1

$R$ (expression level)=$\Delta Ct$ value in cervical cancer patient's tissue−$\Delta Ct$ value in THP-1

The Ct value of the reference gene used in the test represented the Ct value for GAPDH and the reference gene may include another housekeeping gene in addition to GAPDH used in this test.

SKBR3: It may be verified whether hTERT was actually overexpressed as a positive control.

As a result analyzed according to a negative control group which was input in a GraphPad Prism program by using the expression level of hTERT resulted from above and cytopathological separation, 10 or more was positive and 10 or less was negative based on the expression level. Actually, when comparing expression levels of hTERT mRNA in a cytopathological high-level lesion patient group of SCC-HSIL and in a normal patient group, it was verified that the expression level of 10 times or more was shown in two groups. Accordingly, the patient showing the hTERT expression of 10 or less was not shown in the high-level lesion patient group of SCC-HSIL and it was verified that the expression of hTERT was shown as negative of 0 in a low-lesion patient group of ASCUS or less, particularly, a group of normal-high or less (see FIGS. 17 and 18). As such, when the hTERT mRNA qRT-PCR was used, in the case where the high expression rate was shown in the low lesion, the result was obtained as an accurate diagnosis in the high-level lesion as a prediction factor showing a possibility to progress to the cancer and thus, it is considered that more quantified objective data may be indicated in diagnosis and treatment of the patient.

The result of the Example is as follows.

1. Sensitivity for Each Type

As a result of verifying sensitivity for each type, it was verified that the sensitivity was detected in 100 to 10 fg (see FIGS. 4 to 16).

2. Detection of 16 HPV Types Using Multiplex Real-time PCR

In Set I, HPV types 16, 31, 33, 35, 52, and 58 were detected and checked by using FAM dye.

In Set II, HPV types 18, 39, 45, 59, and 68 were detected by using Cy5 dye.

In Set III, HPV types 53, 56, 66, 51, and 69 were detected and checked by using HEX dye (see Table 2).

TABLE 2

| No. | | F2-2(3)mix/R2-1 | | | F2-4/R2 | | | F2-4/R2-1 | | |
|---|---|---|---|---|---|---|---|---|---|---|
| | | set 1 | set 2 | set 3 | set 1 | set 2 | set 3 | set 1 | set 2 | set 3 |
| 1 | HPV-16 | 19.35 | N/A | N/A | 20.45 | 24.89 | N/A | 20.73 | N/A | N/A |
| 2 | HPV-18 | N/A | 25.29 | N/A | 22.46 | 22.57 | N/A | N/A | 22.07 | N/A |
| 3 | HPV-31 | 19.13 | 13.84 | N/A | 18.4 | N/A | N/A | 20.43 | N/A | N/A |
| 4 | HPV-33 | 19.98 | N/A | N/A | 19.85 | N/A | N/A | 19.82 | N/A | N/A |
| 5 | HPV-35 | 19.62 | N/A | N/A | 19.36 | N/A | N/A | 21.48 | N/A | N/A |
| 6 | HPV-39 | N/A | 28.98 | N/A | N/A | 24.72 | N/A | N/A | 26.06 | N/A |
| 7 | HPV-45 | N/A | 26.28 | N/A | N/A | 23.46 | N/A | N/A | 24.36 | N/A |
| 8 | HPV-51 | N/A | N/A | 28.82 | N/A | N/A | 34.89 | N/A | N/A | 29.56 |
| 9 | HPV-52 | 17.57 | N/A | N/A | 18.97 | N/A | 1.84 | 16.81 | N/A | 1.93 |
| 10 | HPV-53 | N/A | N/A | 23.72 | N/A | N/A | 22.71 | N/A | N/A | 22.8 |
| 11 | HPV-54 | N/A | N/A | N/A | N/A | N/A | N/A | N/A | N/A | N/A |
| 12 | HPV-56 | N/A | N/A | 22.78 | N/A | N/A | 23.21 | N/A | N/A | 22.77 |
| 13 | HPV-58 | 19.77 | N/A | N/A | 19.39 | N/A | N/A | 20.74 | N/A | N/A |
| 14 | HPV-59 | N/A | 30.26 | N/A | N/A | 25.22 | N/A | N/A | 26.48 | N/A |
| 15 | HPV-66 | N/A | N/A | 22.27 | N/A | N/A | 19.49 | N/A | N/A | 20.2 |
| 16 | HPV-68 | N/A | 26.5 | N/A | N/A | 25.86 | N/A | N/A | 26.58 | N/A |
| 17 | HPV-69 | 12.55 | N/A | 25.4 | N/A | N/A | 26.24 | N/A | N/A | 26.56 |
| 18 | HPV-06 | N/A | N/A | N/A | N/A | N/A | N/A | N/A | N/A | N/A |
| 19 | HPV-11 | N/A | N/A | N/A | N/A | N/A | N/A | N/A | N/A | N/A |
| 20 | HPV-84 | N/A | N/A | N/A | N/A | N/A | N/A | N/A | N/A | N/A |
| 21 | HPV-87 | N/A | N/A | N/A | N/A | N/A | N/A | N/A | N/A | N/A |

Table 2 illustrates detection of Multiplex real-time PCR according to a HPV type.

3. Verification of Sensitivity in Comparison with Existing Method (Real-time NASBA) in Clinical Test A comparison test with existing Real-time NASBA was performed by targeting a total of 117 specimens of 68 clinical specimens having a result of an existing DNA chip and 49 normal specimens for a specificity test.

As a result, it was verified that the result was not shown in the normal specimens, and in a total of 68 clinical specimens having the cytopathological high-level lesion, the Real-time NASBA (only 5 HPV types of 16, 18, 31, 33, 45 can be detected) was performed. The Real-time NASBA can detect E6/E7 mRNA for each target gene type in the specimens which were positive in an internal control (IC). In 38 specimens among 68 clinical specimens, the IC positive of the real-time NASBA was shown and as a result of detecting the E6/E7 mRNA for each target gene type, the positive rate of 28/38 (73.7%) was shown. The specimen for the gene types which may not be detected in the Real-time NASBA among 10 negative specimens was 5/38 (13.2%), and the specimen which may be detected in Real-time NASBA, but may not be detected was 5/38 (13.2%). On the other hand, in the case of Multiplex Real-time PCR, in 38 specimens which were positive in the real-time NASBA, the positive rate of 38/38 (100%) was verified. Further, even in 30 specimens without detecting the HPV E6/E7 mRNA because the IC was negative in the Real-time NASBA, similarly, it was verified that the positive was shown in 24/30 (80%) when performing the Real-time PCR. As such, it was verified that when performing the Multiplex real-time PCR (62/68, 91.2%), the sensitivity of 50% (34/68) was increased compared to when performing the Real-time NASBA (28/68, 41.2%) (see Table 3).

TABLE 3

| Cytological result Cytology results | DNA chip (Goodgen) DNA chip (Goodgen) | Sample No. Sample No. | Real-time NASBA (biomeriux)U1A, 16, 18, 31, 33, 45 type | | Real time E6-7 PCR Positive rate (%) Real time E6-7 PCR Positive rate (%) |
|---|---|---|---|---|---|
| | | | Positive rate (%) | Negative rate (%) | |
| SCC & ADC | High risk | 15 | 11 (73.3%) | 4 (26.7%) | 15 (100%) |
| HSIL | High risk | 23 | 17 (73.9%) | 6 (26.1%) | 23 (100%) |
| SCC* | High risk | 9 | | 9 (100%) | 9 (100%) |
| HSIL* | High risk | 21 | | 21 (100%) | 15 (71.4%) |
| Normal | Normal | 60 | 0 (0.0%) | 60 (100.0%) | 0 (0%) |

Table 3 illustrates a detection comparison of Real-time NASBA and Multiplex Real-time PCR using HPV mRNA, * specimen as Real-time NASBA Internal control negative 4. Positive Rate and Negative Rate of HPV E6/7 mRNA Multiplex Real-time PCR Using Clinical Specimen As a result of performing the Multiplex Real-time PCR by using 75 specimens which had the high-level lesion in the cytopathological test and infected with the HPV high-risk group in a DNA gene type test (DNA chip), the positive rate was 98.7%, and the negative rate was 1.3%. As a result of performing the Multiplex Real-time PCR by using 110 specimens which were normal in the cytopathological test and not infected with the HPV in a DNA gene type test (DNA chip), the positive rate was 0%, and the negative rate was 100%. As a result, the specificity of the test was 100% and the sensitivity was 98.7%, and thus it was verified that the specificity and the sensitivity were very high compared to an existing testing method (see Table 4).

TABLE 4

HPV mRNA Multiplex Real-time PCR

Clinical Specimens

| Cytologic Test | HPV DNA Chip Test | Positive Positive | Negative Negative | Total Total |
|---|---|---|---|---|
| SCC &HSIL | HPV High-risk Positive | 74 (98.7%) | 1 (1.3%) | 75 (100%) |
| Normal | HPV Negative | 0 (0%) | 110 (100%) | 110 (100%) |

Table 4 illustrates a result of Multiplex Real-time PCR using HPV mRNA separated from the clinical specimen.

5. Comparison of DNA Gene Type Test (DNA Chip) and Specificity of HPV E6/7 mRNA Multiplex Real-time PCR Even in normal cervix, since the HPV DNA positive rate was very high, in order to verify availability of a test targeting mRNA, in the cytopathological test, it was normal. However, in the DNA gene type test (DNA chip), the Multiplex Real-time PCR was performed by using 66 specimens infected with the HPV high-risk group. As a result, it was verified that 6.3% (6/95) was detected and the above positive problem for the DNA chip was reduced (see Table 5).

TABLE 5

| No. | Molecular No. | Cytology | Result (Goodgen kit) | Multiplex |
|---|---|---|---|---|
| 1 | M-11-1392 | — | 16 | 28.95 |
| 2 | M-11-150 | — | 52 | 30.14 |
| 3 | M-11-917 | — | 31 | 32.88 |
| 4 | M-11-551 | — | 58 | undetermined |
| 5 | M-11-672 | — | 16, 33 | undetermined |
| 6 | M-10-1708 | — | 16 | undetermined |
| 7 | M-11-152 | — | 16 | undetermined |
| 8 | M-11-106 | — | 52 | undetermined |
| 9 | M-10-1578 | — | 16 | undetermined |
| 10 | M-11-149 | — | 16 | undetermined |
| 11 | M-10-1299 | — | 58 | undetermined |
| 12 | M-11-119 | — | 35, 66 | 32.54 |
| 13 | M-10-993 | — | 33 | undetermined |
| 14 | M-10-1170 | — | 16 | undetermined |
| 15 | M-10-1517 | — | 58 | undetermined |
| 16 | M-11-52 | — | 16 | undetermined |
| 17 | M-11-94 | — | 31 | undetermined |
| 18 | M-11-104 | — | 33, 58 | undetermined |
| 19 | M-11-253 | — | 16 | undetermined |
| 20 | M-11-286 | — | 16 | undetermined |
| 21 | M-11-287 | — | 16 | undetermined |
| 22 | M-11-327 | — | 16 | undetermined |
| 23 | M-11-389 | — | 33, 58 | undetermined |
| 24 | M-11-466 | — | 16, 18 | undetermined |
| 25 | M-11-467 | — | 16, 18, 39, 58, 68 | undetermined |
| 26 | M-11-486 | — | 16 | undetermined |
| 27 | M-11-605 | — | 18, 58 | undetermined |
| 28 | M-11-617 | — | 16, 18 | undetermined |
| 29 | M-11-623 | — | 33 | undetermined |
| 30 | M-11-633 | — | 16, 18 | undetermined |
| 31 | M-11-696 | — | 33 | undetermined |
| 32 | M-11-742 | — | 18, 35 | undetermined |
| 33 | M-11-925 | — | 16 | undetermined |
| 34 | M-11-858 | — | 58, 68 | undetermined |
| 35 | M-11-948 | — | 16 | undetermined |
| 36 | M-11-964 | — | 16 | undetermined |
| 37 | M-11-986 | — | 58 | undetermined |
| 38 | M-11-993 | — | 16, 58 | undetermined |
| 39 | M-11-1027 | — | 16 | undetermined |
| 40 | M-11-1038 | — | 58 | undetermined |
| 41 | M-11-1042 | — | 16 | undetermined |
| 42 | M-11-1043 | — | 16 | undetermined |
| 43 | M-11-1057 | — | 16, 68 | undetermined |
| 44 | M-11-1059 | — | 58 | undetermined |
| 45 | M-11-1083 | — | 16, 18, 56 | undetermined |
| 46 | M-11-1084 | — | 16 | undetermined |
| 47 | M-11-1087 | — | 16, 18 | undetermined |
| 48 | M-11-1088 | — | 16 | undetermined |
| 49 | M-11-1416 | — | 16, 58 | undetermined |
| 50 | M-11-1454 | — | 16, 18 | undetermined |
| 51 | M-11-1497 | — | 52 | undetermined |
| 52 | M-11-1536 | — | 16, 18, 33 | undetermined |
| 53 | M-11-1543 | — | 16, 39, 66 | undetermined |
| 54 | M-11-1562 | — | 16 | undetermined |
| 55 | M-11-1563 | — | 33 | undetermined |
| 56 | M-11-1637 | — | 16 | undetermined |
| 57 | M-11-1658 | — | 16, 18, 39 | undetermined |
| 58 | M-11-1663 | — | 52 | undetermined |
| 59 | M-11-1669 | — | 16 | undetermined |
| 60 | M-11-1747 | — | 18, 58 | 26.52 |
| 61 | M-11-1748 | — | 16 | undetermined |
| 62 | M-11-1798 | — | 16 | undetermined |
| 63 | M-11-1799 | — | 33 | undetermined |
| 64 | M-11-1812 | — | 16 | undetermined |
| 65 | M-11-1897 | — | 18, 58 | undetermined |
| 66 | M-11-1932 | — | 16 | undetermined |
| 67 | M-11-47 | — | 18 | undetermined |
| 68 | M-10-1056 | — | 66 | 33.3 |
| 69 | M-10-1542 | — | 56 | undetermined |
| 70 | M-10-1651 | — | 45 | undetermined |
| 71 | M-11-69 | — | 45 | undetermined |
| 72 | M-11-73 | — | 56 | undetermined |
| 73 | M-11-239 | — | 59 | undetermined |
| 74 | M-11-241 | — | 18 | undetermined |
| 75 | M-11-328 | — | 18 | undetermined |
| 76 | M-11-460 | — | 68 | undetermined |
| 77 | M-11-472 | — | 18, 56 | undetermined |
| 78 | M-11-523 | — | 18 | undetermined |
| 79 | M-11-729 | — | 18 | undetermined |
| 80 | M-11-738 | — | 18 | undetermined |
| 81 | M-11-846 | — | 18 | undetermined |
| 82 | M-11-919 | — | 18 | undetermined |
| 83 | M-11-1089 | — | 39 | undetermined |
| 84 | M-11-1154 | — | 18 | undetermined |
| 85 | M-11-1535 | — | 45 | undetermined |
| 86 | M-11-1654 | — | 69 | undetermined |
| 87 | M-11-1661 | — | 18 | undetermined |
| 88 | M-11-1718 | — | 66 | undetermined |
| 89 | M-11-1728 | — | 18 | undetermined |
| 90 | M-11-1793 | — | 66 | undetermined |
| 91 | M-11-1808 | — | 68 | undetermined |
| 92 | M-11-1809 | — | 56, 69 | undetermined |
| 93 | M-11-1894 | — | 18 | undetermined |
| 94 | M-11-320 | — | 66 | undetermined |
| 95 | M-11-1880 | — | 56 | undetermined |

Table 5 illustrates a comparison of a DNA chip result using DNA and a Multiplex real-time PCR result using mRNA.

6. Detection Frequency of HPV E6/E7 mRNA Using Multiplex Real-time PCR

Detection frequencies of HPV E6/E7 mRNA using a total of 545 cytopathologically separated samples and 49 histological samples were verified by using the multiplex real-time PCR, respectively. As a result, according to a cytopathological classification, 17/18 (94.4%) in SCC, 20/21 (95.2%) in HSIL, 14/17 (82.4%) in ASC-H, 49/101 (48.5%) in LSIL, 21/100 (21%) in ASC-US, 3/98 (3.1%) in a normal high sample, and 0/198 (0%) in a normal sample were shown as positive (see FIGS. 17 and 18). Further, according to a histological classification, 22/20 (91%) in SCC, 14/16 (88%) in CIN3+, 6/7 (86%) in CIN2+, and 2/4 (50%) in CIN1 were shown as positive, respectively (see FIGS. 17 and 18).

7. Comparison of Expression Level Using hTERT Real-time PCR

The expression of hTERT was verified by targeting specimens resulted from cytopathological and histological tests (see Table 6). As a result of verifying the hTERT expression level, in normal persons, there is no person having the relative expression level of 10 or more, but it was verified that in the high-level lesions of SCC, HSIL, and ASC-H, high expression rate of 10 or more was shown, and the expression level of 10 or more was shown in patients having 40% (40/100) in ASCUS and 35.6% (36/101) in LSIL (see FIG. 19).

TABLE 6

| Cytological diagnosis | Number of samples | Histological diagnosis | Number of samples |
|---|---|---|---|
| SCC | 18 (3.3%) | Sqaumouscarcinoma | 16 (33%) |
| SCC | 18 (3.3%) | Adenocarcinoma | 1 (2%) |
| HSIL | 21 (3.9%) | Sqaumouscarcinoma | 4 (8%) |
| HSIL | 21 (3.9%) | CIN3 | 13 (27%) |
| HSIL | 21 (3.9%) | CIN2 | 3 (6%) |
| ASC-H | 17 (3.1%) | Sqaumous carcinoma | 1 (2%) |
| ASC-H | 17 (3.1%) | CIN3 | 3 (6%) |
| ASC-H | 17 (3.1%) | CIN2 | 4 (8%) |
| ASC-H | 17 (3.1%) | CIN1 | 4 (8%) |
| LSIL | 101 (18.5%) | — | — |
| ASCUS | 100 (18.3%) | — | — |
| Normal-High | 90 (16.5%) | | |
| Normal | 198 (36.3%) | | |
| Total | 545 (100%) | | 49 (100%) |

Table 6 illustrates cytological and histological specimens used in comparison of the expression level of hTERT real-time PCR.

8. Comparison in Positive Rate Between HPV E6/7 mRNA Multiplex Real-time PCR and hTERT Real-time PCR The HPV E6/7 mRNA multiplex real-time PCR was performed by using the same specimen in which the expression was compared by using the hTERT real-time PCR and positive rates of two methods were compared. As a result, through the cytological classification, in SCC, the positive expression was shown in all of 16 specimens (88.9%) among a total of 18 specimens, and one specimen of two specimens had the positive rate in the HPV E6/7 mRNA PCR and the other specimen thereof had the positive rate in the hTERT real-time PCR. In addition, in HSIL, 20 (95.2%) specimens of 21 specimens were positive in the two methods, but one specimen was positive only in the hTERT real-time PCR. In ASCUS-High, 14 (82.4%) specimens of 17 specimens were positive in the two methods and the remaining three specimens were positive only in the hTERT real-time PCR. In ASCUS, only 6 (6%) specimens of a total of 100 specimens were positive in the two methods, 34 specimens have the positive expression rate only in the hTERT real-time PCR, 15 specimens were positive only in the HPV E6/7 mRNA multiplex real-time PCR, and the remaining 45 specimens were negative. In LSIL, 16 (15.8%) specimens of 101 specimens were positive in the two methods, 18 specimens had the positive expression rate only in the hTERT real-time PCR, 33 specimens were positive only in the HPV E6/7 mRNA multiplex real-time PCR, and the rest of 34 specimens were negative (see Table 7). Further, 20 specimens (90.9%) of total 22 specimens in SCC were positive in the two methods through a histological classification and the rest of two specimens were positive only in the hTERT expression. In addition, in CIN3, 14 specimens (87.5%) of 16 specimens were positive in the two methods and the rest of two specimens (12.5%) were positive only in the hTERT expression, and in CIN2, 6 specimens (85.7%) of total 7 specimens were positive in the two methods and the rest of one specimen (14.3%) was positive only in the hTERT. Further, in CIN1, 2 specimens (50%) of total 4 specimens were positive in the two methods and the rest of 2 specimens (50%) were positive only in the hTERT (see Table 8).

It was verified that the expression of hTERT mRNA was increased in a high-level lesion group sample of ASC-H (P=0.928) and HSIL/SCC (P=0.817) patients compared with a normal group sample. Further, in low-level lesions such as LSIL and ASC-US, as compared with the Real-time PCR method, specimens showing the positive rate of CIN2+ or more were 9/43 (20.9%) in both the HPV E6/E7 and hTERT mRNA methods, 20/43 (46.5%) only in the HPV E6/E7 mRNA PCR method, and 12/43 (27.9%) only in the hTERT mRNA PCR method. Further, as a result of comparing the Real-time PCR method and the HPV DNA test method including the three methods, when simultaneously performing the HPV E6/E7 mRNA PCR method and the hTERT mRNA PCR method having the positive rate of 41/43 (95.3%) and 30/43 (69.8%), it was verified that the higher sensitivity than the HPV DNA method was shown (see Table 9). In the result, as a result of comparing and testing the HPV DNA method and the HPV mRNA E6/E7 method by using 98 specimens which were normal in the cytopathological classification, in the HPV DNA method (HPV DNA genotype (Goodgene, Seoul, Korea), 98/98 (100%) was positive, in the REBA HPV-ID (M&D, Wonju, Korea), 61/98(62.2%) was positive, but in the HPV mRNA E6/E7 method, only 3/98 (3.1%) was positive. Accordingly, in the HPV DNA method, the sensitivity was excellent, but the specificity was bad, it was verified that the HPV DNA method may not be used as the diagnosis method for the high-level lesion (causing the cancer) including the cancer. Other diagnosis methods (the HPV mRNA E6/E7 method and the HPV hTERT mRNA method) which may replace the HPV DNA method were required. In the high-level lesions such as SCC, HSIL, and ASCUS-High, when simultaneously performing two methods compared with only the real-time PCR, the positive rate of 100% was shown, and even in low-level lesions such as LSIL or ASC-US, the positive rate of 95% or more was shown. Further, as the cell lesion was decreased, in the HPV E6/7 mRNA multiplex real-time PCR, the positive rate was shown compared to the hTERT real-time PCR, and thus it was verified again that the hTERT mRNA method was used as an important marker causing overexpression in the cancer. Therefore, the hTERT real-time PCR was additionally diagnosed to be useful for cervical cancer diagnosis as a prediction factor capable of predicting a possibility to progress to the cancer.

TABLE 7

| | | hTERT positive | | hTERT negative | |
|---|---|---|---|---|---|
| | | HPV E6/7 positive | HPV E6/7 negative | HPV E6/7 positive | HPV E6/7 negative |
| SCC | | 16/18 (88.9%) | 1/18 (5.6%) | 1/18 (5.6%) | |
| HSIL | | 20/21 (95.2%) | 1/21 (4.8%) | | |
| ASCUS-H | | 14/17 (82.4%) | 3/17 (17.6%) | | |

TABLE 7-continued

|  | hTERT positive | | hTERT negative | |
|---|---|---|---|---|
|  | HPV E6/7 positive | HPV E6/7 negative | HPV E6/7 positive | HPV E6/7 negative |
| LSIL | 16/101 (15.8%) | 18/101 (17.8%) | 33/101 (32.7%) | 34/101 (33.7%) |
| ASCUS | 6/100 (6%) | 34/100 (34%) | 15/100 (15%) | 45/100 (45%) |
| Total | 74/256 (28.9%) | 55/218 (25.2%) | 48/201 (23.9%) | 79/201 (39.3%) |

Table 7 illustrates a comparison in positive rate between HPV E6/7 mRNA multiplex real-time PCR and hTERT real-time PCR according to a cytological classification.

TABLE 8

|  | hTERT positive | | hTERT negative | |
|---|---|---|---|---|
|  | HPVE6/E7 positive | HPV E6/E7 negative | HPV E6/E7 positive | HPVE6/E7 negative |
| SCC | 20/22 (90.9%) | 2/22 (9.1%) | 0/0 (0) | 0/0 (0) |
| CIN3 | 14/16 (87.5%) | 2/16 (12.5%) | 0/0 (0) | 0/0 (0) |
| CIN2 | 6/7 (85.7%) | 1/7 (14.3%) | 0/0 (0) | 0/0 (0) |
| CIN1 | 2/4 (50%) | 2/4 (50%) | 0/0 (0) | 0/0 (0) |

Table 8 illustrates a comparison in positive rate between HPV E6/7 mRNA multiplex real-time PCR and hTERT real-time PCR according to a histological classification.

TABLE 9

|  |  | Real-time PCR | | | | |
|---|---|---|---|---|---|---|
| Cytology | Histology | All + | HPV E6/7 + hTERT+ | hTERT + | HPV E6/7+ | HPV DNA test |
| LSIL | SCC (n = 10) | 9 (90%) | 2 (20%) | 3 (30%) | 4 (40%) | 8 (80%) |
| LSIL | CIN3 (n = 8) | 8 (100%) | 3 (37.5%) | 1 (12.5%) | 4 (50%) | 6 (75%) |
| LSIL | CIN2 (n = 7) | 6 (85.7%) | 2 (28.6%) | 1 (14.3%) | 3 (42.9%) | 6 (85.7%) |
| LSIL | CIN1 (n = 27) | 27 (100%) | 7 (25.9%) | 10 (37%) | 10 (37%) | 23 (85.2%) |
| LSIL | ND (n = 17) | 17 (100%) | 3 (17.6%) | 4 (23.5%) | 10 (58.8%) | 14 (82.4%) |
| ASC-US | SCC (n = 9) | 9 (100%) | 2 (22.2%) | 4 (44.4%) | 3 (33.3%) | 4 (44.4%) |
| ASC-US | CIN3 (n = 7) | 7 (100%) | 0 | 3 (42.9%) | 4 (57.1%) | 5 (71.4%) |
| ASC-US | CIN2 (n = 2) | 2 (100%) |  |  | 2 (100%) | 1 (50%) |
| ASC-US | CIN1 (n = 11) | 11 (100%) | 4 (36.4%) | 5 (45.5%) | 2 (18.2%) | 9 (81.8%) |
| ASC-US | ND (n = 27) | 27 (100%) | 3 (11.1%) | 19 (70.4%) | 5 (18.5%) | 20 (74.1%) |
| Total |  | 125 | 123 (98.4%) | 26 (18.4%) | 50 (40%) | 47 (37.6%) | 96 (76.8%) |

Table 9 illustrates a comparison in positive rate according to cytopathological and histological classifications by using a Real-time PCR method and a HPV DNA method in low-level lesions (LSIL and ASC-US).

The invention claimed is:

1. A method for increasing the likelihood of making a positive cervical cancer diagnosis, comprising:
   a) separating a total RNA from cells obtained from a specimen;
   b) synthesizing cDNA from a separated total RNA;
   c) performing a multiplexed real-time-PCR for the synthesized cDNA by using a primer set and a detection probe capable of amplifying and detecting HPV high-risk types 16, 35, 31, 58, 33, and 52; a primer set and a detection probe capable of amplifying and detecting HPV high-risk types 18, 45, 39, 68, and 59; a primer set and a detection probe capable of amplifying and detecting HPV high-risk types 53, 56, 66, 51, 69, 26, and 30; a primer set and a detection probe capable of amplifying and detecting glyceraldehyde 3-phosphate dehydrogenase (GAPDH) as a reference gene; and a primer set and a detection probe capable of amplifying and detecting the human telomerase reverse transcriptase (hTERT) gene as a prognosis marker for the cervical cancer;
   d) detecting an expression level of an amplified HPV high-risk type and quantifying the expression level of the amplified HPV high-risk type based on an expression level of GAPDH; and
   e) comparing an expression level of the hTERT gene in the specimen with an expression level of the hTERT gene in a normal person after quantifying the expression level of the hTERT gene in the specimen based on the expression level of GAPDH,
   wherein an expression level of the hTERT gene in the specimen that is higher than the expression level of the hTERT gene in a normal person increases the likelihood that a specimen also having a detected expression level of an amplified HPV high-risk type is indicative of a positive cervical cancer diagnosis.

2. The method of claim 1, wherein the primer set capable of amplifying the HPV high-risk types 16, 35, 31, 58, 33, and 52 are represented by SEQ ID NOS: 1 and 2 and the detection probe has a base sequence represented by SEQ ID NO: 3.

3. The method of claim 1, wherein the primer set capable of amplifying the HPV high-risk types 18, 45, 39, 68, and 59 are represented by SEQ ID NOS: 4, 5, 6 and 7 and the detection probe has a base sequence represented by SEQ ID NO: 8.

4. The method of claim 1, wherein the primer set capable of amplifying the HPV high-risk types 53, 56, 66, 51, 69, 26, and 30 are represented by SEQ ID NOS: 9 and 10 or 12 and 13 and the detection probe has a base sequence represented by SEQ ID NO: 11 or 14.

5. The method of claim 1, wherein the primer set capable of amplifying the GAPDH gene are represented by SEQ ID NOS: 15 and 16 and the detection probe has a base sequence represented by SEQ ID NO: 17, and the primer set capable of amplifying the hTERT gene are represented by SEQ ID NOS: 18 and 19 and the detection probe has a base sequence represented by SEQ ID NO: 20.

* * * * *

SEQUENCE LISTING

<160> NUMBER OF SEQ ID NOS: 20

<210> SEQ ID NO 1
<211> LENGTH: 29
<212> TYPE: DNA
<213> ORGANISM: Artificial Sequence
<220> FEATURE:
<223> OTHER INFORMATION: F primer

<400> SEQUENCE: 1
ttagatttrb adcchgarvc aactgayct                                    29

<210> SEQ ID NO 2
<211> LENGTH: 22
<212> TYPE: DNA
<213> ORGANISM: Artificial Sequence

```
<220> FEATURE:
<223> OTHER INFORMATION: R primer

<400> SEQUENCE: 2
cyggttbtgc ttgtccakct gg                                                    22

<210> SEQ ID NO 3
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (17)
<223> OTHER INFORMATION: n= a or g or c or t

<400> SEQUENCE: 3
ctgytatgag caattrnvyg rcagctcaga                                            30

<210> SEQ ID NO 4
<211> LENGTH: 23
<212> TYPE: DNA
<213> ORGANISM: Artificial Sequence
<220> FEATURE:
<223> OTHER INFORMATION: F primer

<400> SEQUENCE: 4
gamattgtdt trsatttrkr dcc                                                   23

<210> SEQ ID NO 5
<211> LENGTH: 22
<212> TYPE: DNA
<213> ORGANISM: Artificial Sequence
<220> FEATURE:
<223> OTHER INFORMATION: F primer

<400> SEQUENCE: 5
tgcargamat tgtrttrsak tt                                                    22

<210> SEQ ID NO 6
<211> LENGTH: 28
<212> TYPE: DNA
<213> ORGANISM: Artificial Sequence
<220> FEATURE:
<223> OTHER INFORMATION: F primer

<400> SEQUENCE: 6
tgcargamat tgtdttrsak ttrkrdcc                                              28

<210> SEQ ID NO 7
<211> LENGTH: 29
<212> TYPE: DNA
<213> ORGANISM: Artificial Sequence
<220> FEATURE:
<223> OTHER INFORMATION: R primer

<400> SEQUENCE: 7
tgtgacgytg tkgttcrkcy cgtckrgct                                             29

<210> SEQ ID NO 8
<211> LENGTH: 25
<212> TYPE: DNA
<213> ORGANISM: Artificial Sequence
<220> FEATURE:
<223> OTHER INFORMATION: probe
```

<400> SEQUENCE: 8
ttgacctkbt rtgyyacgag caatt       25

<210> SEQ ID NO 9
<211> LENGTH: 24
<212> TYPE: DNA
<213> ORGANISM: Artificial Sequence
<220> FEATURE:
<223> OTHER INFORMATION: F primer

<400> SEQUENCE: 9
trtwttagaa ctdryaccdc aaac        24

<210> SEQ ID NO 10
<211> LENGTH: 29
<212> TYPE: DNA
<213> ORGANISM: Artificial Sequence
<220> FEATURE:
<223> OTHER INFORMATION: R primer

<400> SEQUENCE: 10
gtctayttca tcctcatcct cytcctctg   29

<210> SEQ ID NO 11
<211> LENGTH: 29
<212> TYPE: DNA
<213> ORGANISM: Artificial Sequence
<220> FEATURE:
<223> OTHER INFORMATION: probe

<400> SEQUENCE: 11
ttgacctrca dtgchatgag caattgrac   29

<210> SEQ ID NO 12
<211> LENGTH: 23
<212> TYPE: DNA
<213> ORGANISM: Artificial Sequence
<220> FEATURE:
<223> OTHER INFORMATION: F primer

<400> SEQUENCE: 12
gatgtwrtat trsatttrry rcc         23

<210> SEQ ID NO 13
<211> LENGTH: 27
<212> TYPE: DNA
<213> ORGANISM: Artificial Sequence
<220> FEATURE:
<223> OTHER INFORMATION: R primer

<400> SEQUENCE: 13
acgcayatta tctryttcat cctcmtc     27

<210> SEQ ID NO 14
<211> LENGTH: 29
<212> TYPE: DNA
<213> ORGANISM: Artificial Sequence
<220> FEATURE:
<223> OTHER INFORMATION: probe

<400> SEQUENCE: 14
ttgacytrca vtgytacgar caattkgac   29

```
<210> SEQ ID NO 15
<211> LENGTH: 22
<212> TYPE: DNA
<213> ORGANISM: Artificial Sequence
<220> FEATURE:
<223> OTHER INFORMATION: F primer

<400> SEQUENCE: 15
ccatcttcca ggagcgagat cc                                              22

<210> SEQ ID NO 16
<211> LENGTH: 21
<212> TYPE: DNA
<213> ORGANISM: Artificial Sequence
<220> FEATURE:
<223> OTHER INFORMATION: R primer

<400> SEQUENCE: 16
atggtggtga agacgccagt g                                               21

<210> SEQ ID NO 17
<211> LENGTH: 24
<212> TYPE: DNA
<213> ORGANISM: Artificial Sequence
<220> FEATURE:
<223> OTHER INFORMATION: probe

<400> SEQUENCE: 17
tccacgacgt actcagcgcc agca                                            24

<210> SEQ ID NO 18
<211> LENGTH: 22
<212> TYPE: DNA
<213> ORGANISM: Artificial Sequence
<220> FEATURE:
<223> OTHER INFORMATION: F primer

<400> SEQUENCE: 18
tgacgtccag actccgcttc at                                              22

<210> SEQ ID NO 19
<211> LENGTH: 23
<212> TYPE: DNA
<213> ORGANISM: Artificial Sequence
<220> FEATURE:
<223> OTHER INFORMATION: R primer

<400> SEQUENCE: 19
ttctggctcc cacgacgtag tcc                                             23

<210> SEQ ID NO 20
<211> LENGTH: 25
<212> TYPE: DNA
<213> ORGANISM: Artificial Sequence
<220> FEATURE:
<223> OTHER INFORMATION: probe

<400> SEQUENCE: 20
acgggctgcg gccgattgtg aacat                                           25
```